(12) United States Patent
Bau et al.

(10) Patent No.: US 8,877,518 B2
(45) Date of Patent: Nov. 4, 2014

(54) MULTIPLEXED NANOSCALE ELECTROCHEMICAL SENSORS FOR MULTI-ANALYTE DETECTION

(75) Inventors: Haim H. Bau, Swarthmore, PA (US); Michael Schrlau, Drexel Hill, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1278 days.

(21) Appl. No.: 12/526,118

(22) PCT Filed: Feb. 4, 2008

(86) PCT No.: PCT/US2008/001554
§ 371 (c)(1),
(2), (4) Date: Sep. 16, 2010

(87) PCT Pub. No.: WO2008/130463
PCT Pub. Date: Oct. 30, 2008

(65) Prior Publication Data
US 2011/0027913 A1 Feb. 3, 2011

Related U.S. Application Data

(60) Provisional application No. 60/888,375, filed on Feb. 6, 2007.

(51) Int. Cl.
*G01N 33/551* (2006.01)
*G01N 33/543* (2006.01)
*G01N 27/30* (2006.01)

(52) U.S. Cl.
CPC .......... *G01N 27/308* (2013.01); *G01N 33/5438* (2013.01); *G01N 33/54313* (2013.01)
USPC ............ 436/524; 436/518; 436/149; 422/50; 422/68.1; 422/82.01; 435/7.1; 435/283.1; 435/287.1; 435/287.2

(58) Field of Classification Search
USPC ........... 436/524; 435/7.1, 283.1, 287.1, 287.2
See application file for complete search history.

(56) References Cited

U.S. PATENT DOCUMENTS

| | | | |
|---|---|---|---|
| 6,241,701 B1 * | 6/2001 | Hofmann | 604/21 |
| 6,525,481 B1 * | 2/2003 | Klima et al. | 315/111.21 |
| 7,456,021 B2 * | 11/2008 | Brant et al. | 436/37 |
| 7,563,614 B2 * | 7/2009 | Orwar et al. | 435/286.2 |
| 8,232,074 B2 * | 7/2012 | Jardemark et al. | 435/29 |
| 2002/0179446 A1 * | 12/2002 | Kasai et al. | 204/453 |
| 2002/0182627 A1 * | 12/2002 | Wang et al. | 435/6 |
| 2003/0218224 A1 | 11/2003 | Schlaf et al. | |
| 2004/0000481 A1 * | 1/2004 | Goudberg et al. | 204/461 |

(Continued)

FOREIGN PATENT DOCUMENTS

JP          60252253         12/1985

OTHER PUBLICATIONS

Albert et al., "Automatic Decoding of Sensor Types Within Randomly Ordered, High-Density Optical Sensor Arrays", Analytical and Bioanalytical Chemistry, Apr. 2002, 373(8), 792-802.

(Continued)

*Primary Examiner* — Melanie Y Brown
(74) *Attorney, Agent, or Firm* — Baker & Hostetler LLP

(57) ABSTRACT

Provided are nanoscale devices suitable for multiplexed, parallel detection of multiple analytes and methods for fabricating such devices.

19 Claims, 12 Drawing Sheets

(56) References Cited

U.S. PATENT DOCUMENTS

| | | | |
|---|---|---|---|
| 2004/0022677 A1* | 2/2004 | Wohlstadter et al. | 422/52 |
| 2006/0013543 A1* | 1/2006 | Walt et al. | 385/101 |
| 2006/0014155 A1 | 1/2006 | Hamers et al. | |
| 2006/0069386 A1* | 3/2006 | Dubnack et al. | 606/41 |
| 2006/0115971 A1 | 6/2006 | Bau et al. | |
| 2006/0121531 A1 | 6/2006 | Wei et al. | |
| 2006/0145194 A1 | 7/2006 | Barron et al. | |
| 2007/0066934 A1* | 3/2007 | Etheredge et al. | 604/46 |
| 2009/0325215 A1* | 12/2009 | Okano et al. | 435/29 |

OTHER PUBLICATIONS

Bowden et al., "Development of a Microfluidic Platform With an Optical Imaging Microarray Capable of Attornolar Target DNA detection", Analytical Chemistry, Sep. 1, 2005, 77(17), 5583-5588.

Breckpot et al., "Exploiting Dendritic Cells for Cancer Immunotherapy: Genetic Modification of Dendritic Cells", J. Gene Med., Nov. 6, 2004, 6(11), 1175-1188.

Cai et al., "Highly Efficient Molecular Delivery into Mammalian Cells Using Carbon Nanotube Spearing", Nature Methods, Jun. 2005, 2(6), 449-454.

Chen et al., "Noncovalent Sidewall Functionalization of Single-Walled Carbon Nanotubes for Protein Immobilization", J. Am. Chem. Soc., Apr. 25, 2001, 123(26), 3838-3839.

Christodoulides et al., "Application of Microchip Assay System for the Measurement of C-reactive Protein in Human Saliva", Lab Chip, Mar. 2005, 5(3), 261-269.

Epstein et al "Combinaton Decoding: An Approach for Univesal DNA Array Fabricaton" J. Am. Chem. Soc., Oct. 21, 2003, 125(45), 13753-13759.

Fulton et al., "Advanced Multiplexed Analysis with the FlowMetrix System", Clinical Chemistry, Sep. 1997, 43(9), 1749-1756.

Kam et al., "Nanotube Molecular Transporters: Internalization of Carbon-Protein Conjugates Into Mammalian Cells", J. Am. Chem. Soc., May 13, 2004, 126(22), 6850-6851.

Karhanek et al., "Single Dna Molecule Detection Using Nanopipettes and Nanoparticles", Nano Letters, Jan. 25, 2005, 5(2), 403-407.

Kikuchi et al., "Genetically Modified Dendritic Cells for Therapeutic Immunity", Tohoku J. Exp. Med., Jan. 2006, 208(1), 1-8.

Kim et al., "The Fabrication of Integrated Carbon Pipes With Sub-Micron Diameters", Nanotechnology, IOP, Bristol, GB, Aug. 1, 2005, 16(8), 1317-1320.

King, "Gene Delivery to Mammalian Cells by Microinjection", Methods Mol. Biol., (no month available) 2004, 245(2), 167-174.

Koehne et al., "The Fabrication and Electrochemical Characterization of Carbon Nanotube Nanoelectrode Arrays", J. Mater. Chem., Nov. 2003, 14(4), 676-684.

Kouklin et al., "Carbon Nanotube Probes for Single-Cell Experimentation and Assays", Appl. Phys. Letter, Oct. 2005, 87(17), 173901-1-173801-3.

Liu et al., "The Dielectrophoresis of Cylindrical and Spherical Particles Submerged in Shells and Semi-Infinite Media", Physics of Fluids, May 2004, 16(5), 1217-1228.

Lundgvist et al., "Gene-Modified Dendritic Cells for Immunotherapy Against Cancer", Med. Oncol., Dec. 2002, 19(4), 197-211.

McKnight et al., "Intracellular Integration of Synthetic Nanostructures with Viable Cells for Controlled Biochemical Manipulation", Nanotechnology, Apr. 2003, 14(5), 551-556.

Michael et al., "Randomly Ordered Addressable High-Density Optical Sensor Arrays", Analytical Chemistry, Apr. 1, 1998, 70(7), 1242-1248.

Naguib et al., "Effect of Carbon Nanofibre Structure on the Binding of Antibodies", Nanotechnology, Apr. 2005, 16(4), 567-571.

Riegelman "Controlled Nanoassembly and Construction of Nanofluidic Devices", Transactions of ASME, J Fluid Engineering, Jan. 2006, 128, 6-13.

Tsulaia et al., "Glass Needle-Mediated Microinjection of Macromolecules and Trangenes into Primary Human Mesenchymal Stem Cells", J. Biomed. Sci., Jan. 2003, 10(3), 328-336.

Tu et al., "Carbon Nanotubes Bases Nanoelectrode Arrays: Fabrication, Evaluation, and Application in Voltammetric Analysis", Electroanalysis, Jan. 2005, 17(1), 79-84.

Walt et al., "Techview: Molecular Biology. Bead-Based Fiber-Optic Arrays", Science, Jan. 21, 2000, 287(5452), 451-452.

Wong et al., "Optical Fiber Tip Fabricated by Surface Tension Controlled Etching", Solid-State Sensor, Actuator and Microsystems Workshop, Hilton Head Island, SC, Jun. 2-6, 2002, 94-97.

Zhang et al., "An Integrated Nitric Oxide Sensor Based on Cabon Fiber Coated with Selective Membranes", Electroanalysis, Oct. 2000, 12(14), 1113-1117.

\* cited by examiner (i)

(ii)

MULTIPLEXED NANOSCALE ELECTROCHEMICAL SENSORS FOR MULTI-ANALYTE DETECTION

CROSS-REFERENCE TO RELATED APPLICATIONS

This application is the National Stage of International Application No. PCT/US2008/001554, filed Feb. 4, 2008, which claims the benefit of U.S. Provisional Application No. 60/888,375, filed Feb. 4, 2007, the disclosures of which are incorporated herein by reference in their entirety.

FIELD OF THE INVENTION

The disclosed invention relates to the field of electrochemical sensors. The present invention also relates to the field of microscale devices.

BACKGROUND OF THE INVENTION

Various scientific and patent publications are referred to herein. Each is incorporated by reference in its entirety.

To monitor the health of patients, identify infectious diseases, screen for cancer, and monitor the safety of water and food supplies, it is often desirable or even necessary to concurrently detect and measure the concentrations of multiple analytes in a given sample. Such analytes can include various chemicals, proteins, viruses, DNA, RNA, cells, bacteria, antibodies, and other biological and non-biological markers.

It is known that accurate and reliable biomarker-based cancer screening requires the concurrent quantification of multiple proteins, and, in certain cases, can entail the establishment of a gene profile of cancer and pre-cancer cells. In the latter case, one takes advantage of the fact that precancerous and cancerous cells exhibit a change in the transcription levels of many genes. Accordingly, the detection of the deviations in mRNA levels provides an informative target for cancer diagnostics. Establishing a gene profile, however, requires the quantification of from about 10 to about 30 genes, which quantification, in turn, is most efficiently accomplished by the use of an array of multiple sensors.

Existing devices for performing such analyses have certain drawbacks, and often require the use of large, complex devices, including cameras, fluorescence meters, optical scanners, and the like. The size and complexity of such devices renders optical detection techniques ill-suited for use in portable devices.

Because of the limitations inherent in multiple analyte detection systems that rely on optical detection, there is a need for devices capable of detecting multiple analytes on a non-optical basis. There is also a related need for methods of fabricating such devices.

SUMMARY OF THE INVENTION

The general description and the following detailed description are exemplary and explanatory only and are not restrictive of the invention, as defined in the appended claims. Other aspects of the present invention will be apparent to those skilled in the art in view of the detailed description of the invention as provided herein.

In one aspect, the present invention provides devices, comprising: a capillary, wherein the capillary is capable of being electrically addressed; and at least one particle adjacent to the capillary.

In another aspect, the present invention provides devices, comprising: a substrate, wherein the substrate comprises a surface and a plurality of electrodes, wherein at least one of the electrodes is capable of being individually electrically addressed; and at least one particle comprising at least one functionality, wherein at least one particle comprising at least one functionality is adjacent to at least one electrode capable of being electrically addressed.

Further provided are methods, comprising: contacting a plurality of individually addressable and spatially distributed conductive capture electrodes with a plurality of particles dispersed in a carrier medium, wherein each of the particles comprises at least one sensing functionality, at least one barcode functionality, or any combination thereof; wherein contacting a conductive capture electrode with the plurality of particles dispersed in the carrier medium gives rise to at least one particle being positioned adjacent to at least one conductive capture electrode by action of capillary forces, surface forces, Van der Waals forces, electrokinetic forces, electromagnetic forces, or any combination thereof; and identifying the spatial location of one or more particles positioned adjacent to at least one individually addressable and spatially distributed capture electrode.

Additionally provided are methods, comprising: contacting a first fluid with a plurality of conductive capture electrodes, wherein at least one of the conductive capture electrodes is capable of being individually electrically addressed; flowing a second fluid adjacent to the first fluid, wherein the second fluid resides between the first fluid and a director electrode and comprises a plurality of particles, wherein each of the particles comprise one or more functionalities; and applying an electric potential between the director electrode and the plurality of conductive capture electrodes so as to give rise to at least one particle of the second fluid being positioned adjacent to at least one conductive capture electrode.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings.

DETAILED DESCRIPTION OF ILLUSTRATIVE EMBODIMENTS

Figure 1:
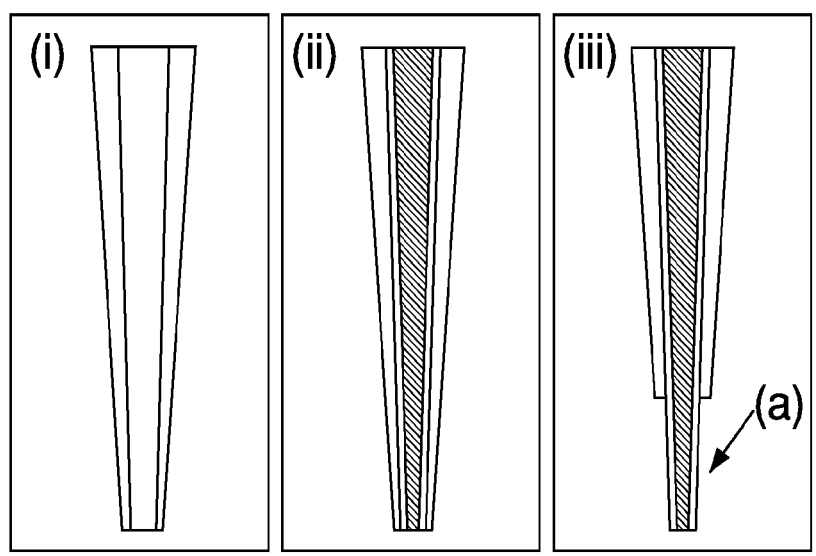
FIG. 1 illustrates the phases of fabricating a nanoscale carbon electrode—FIG. 1(*i*) depicts a pulled quartz pipette, FIG. 1(*ii*) depicts carbon deposited within the pipette, and FIG. 1(*iii*), at (a), illustrates carbon electrode exposed after a portion of the quartz pipette is etched away.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

As employed above and throughout the disclosure, the following terms, unless otherwise indicated, shall be understood to have the following meanings.

TERMS

"Adjacent" refers to two or more entities, such as objects, surfaces, or any combination thereof, that reside near, next to, or are in contact with each other and are physically, electrically, or any combination thereof, and may be affected by their proximity to each other. "Directly adjacent" means two or more objects that are in contact with one another.

"Barcode" refers to an aspect or characteristic of an object that is capable of assisting with identifying that object or identifying that object's location.

"Electrical connection" refers to two or more entities, such as objects, surfaces, or any combination thereof, wherein a change in the electrical characteristics of one or more of the entities is capable of affecting or of being detected by one or more of the other entities.

"Electrode" means an object or site capable of passing an electrical current or a magnetic field. The term can also mean an object or site capable of projecting an electrical potential or current or a magnetic field.

In one aspect, the present invention provides devices, comprising: a capillary, wherein the capillary is capable of being electrically addressed; and at least one particle adjacent to the capillary.

Suitable capillaries comprise conducting materials, semiconducting materials, dielectric materials, or any combination thereof. Conductive materials are considered especially suitable.

Suitable capillary materials include carbon, gold, silver, platinum, aluminum, copper, nickel, chromium, indium, tin, or any combination thereof. Other suitable metals will be known to those of ordinary skill in the art. Electrically conductive polymers are also suitable capillary materials.

Figure 2:
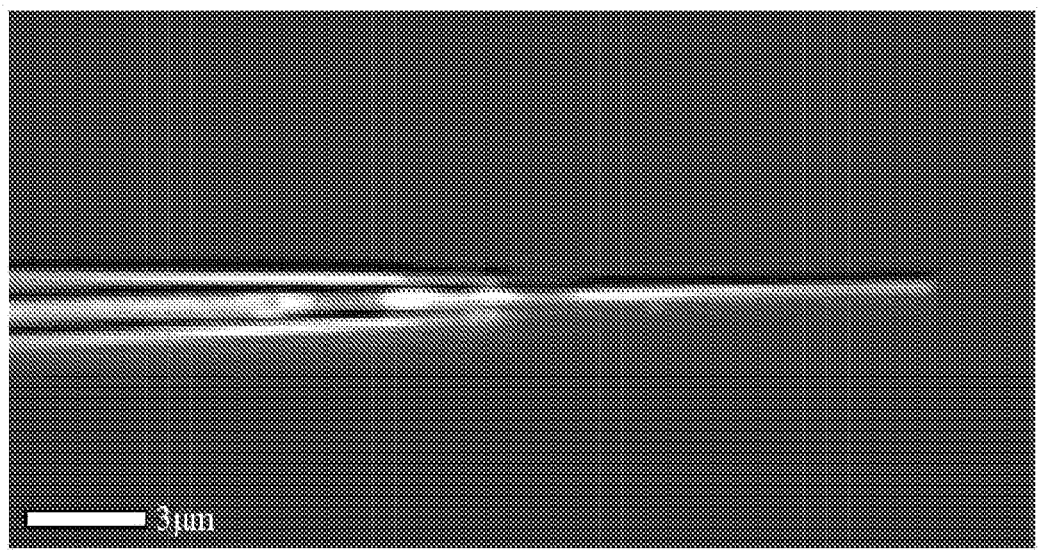
FIG. 2 is an optical micrograph of a nanoelectrode suitable for use in the present invention.

Capillaries produced by the method of Bau, et al., as described in U.S. patent application Ser. No. 11/231,425, filed on Sep. 21, 2005, are particularly suitable for the present invention. Capillaries made according to that method are produced by direct chemical vapor deposition ("CVD") inside a pulled quartz or glass capillary and subsequent etching of the quartz or glass tip to expose a predetermined length of carbon capillary. FIG. 1 depicts this process: FIG. 1(*i*) depicts a pulled quartz capillary; FIG. 1(*ii*) depicts carbon that has been deposited by CVD on the inner surface of the capillary so as to form a carbon capillary residing within the pulled quartz capillary. and FIG. 1(*iii*) depicts the exposed carbon capillary after a portion of the quartz capillary has been etched away. Such a capillary is shown in FIG. 2.

Figure 3:
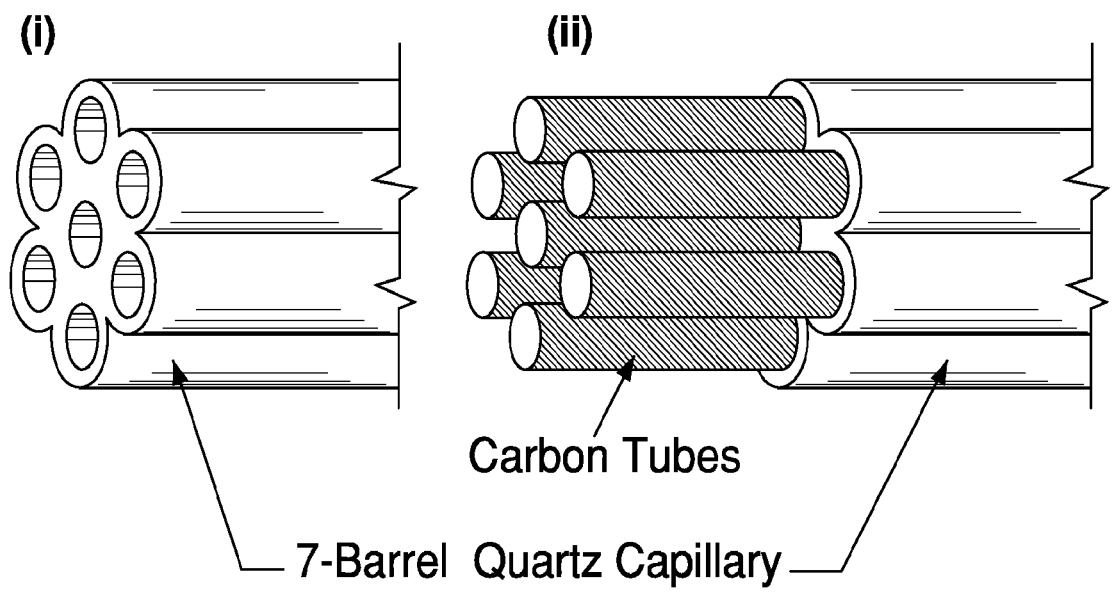
FIG. 3(*i*) depicts a cross-section of a 7-barrel quartz capillary with catalyst-laden inner diameters, FIG. 3(*ii*) depicts a 7-electrode carbon pipette after chemical vapor deposition of the carbon and etching of the quartz capillary.

The technique of Bau, et al., is capable of producing multiple carbon capillaries by CVD of carbon into a multi-barrel quartz pipette structure, as shown in FIGS. 3(*i*) and 3(*ii*).

Figure 4:
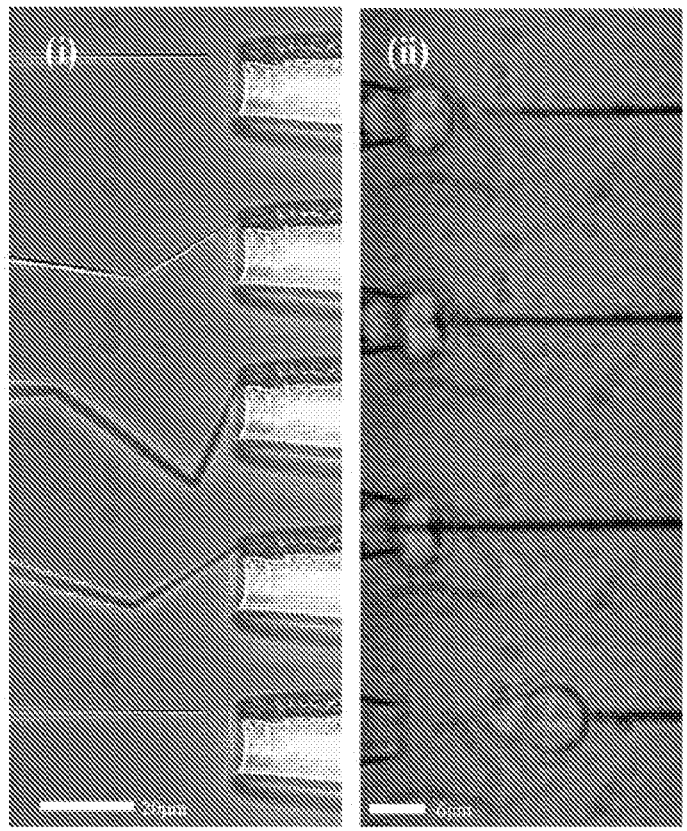
FIG. 4(*i*) is an optical micrograph taken over a time span of about 2.5 seconds of a carbon nanopipette suitable for use in the present invention returning to its original shape after being deformed 90° against a hard surface, and FIG. 4(*ii*) is an optical micrograph of a carbon nanopipette penetrating a cell membrane.
Figure 5:
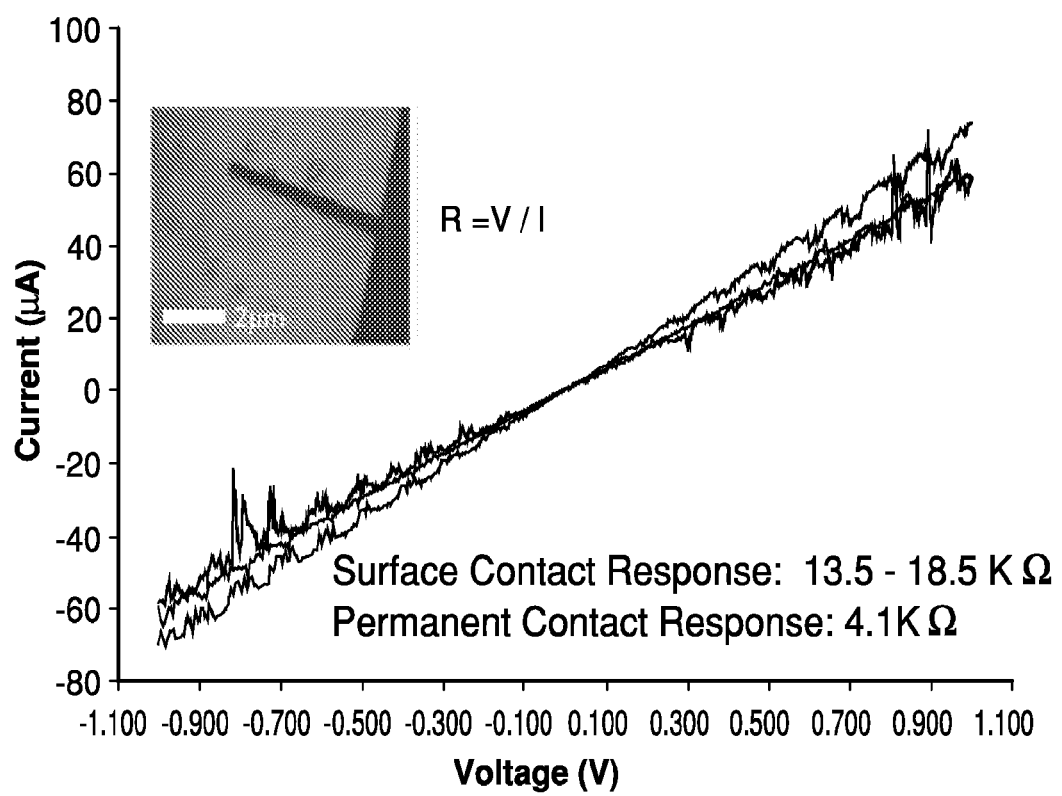
FIG. 5 depicts the resistance behavior of three different nano-scale carbon capillaries, the inset is a photomicrograph of a single carbon capillary.

The resulting capillary structures are biocompatible and display high flexibility. As shown in FIG. 4, carbon capillaries produced by the method of Bau, et al., are capable of bending about 90° and returning to their original shape. Such capillaries also, see FIG. 5, exhibit Ohmic resistance from tip to tail.

Suitable capillaries have lumen diameters in the tens of nanometers up to the micrometer range; lumen diameters can be in the range of from about 10 nm to about 100 micrometers, or from about 20 nm to about 50 micrometers. The wall thickness of the capillaries can be in the range of from about 1 nm to about 1000 nm, and are in the range of from about 100 to about 500 nm, or in the range of from about 10 nm to about 50 nm. Wall thicknesses in the range of about 30 nm are also suitable.

In some embodiments, the capillary and at least one adjacent particle are in electrical connection with one another. It is contemplated that the capillary is capable of detecting a signal related to the binding of one or more functionalities of the particle to one or more analytes to which the particle is contacted.

Figure 6:
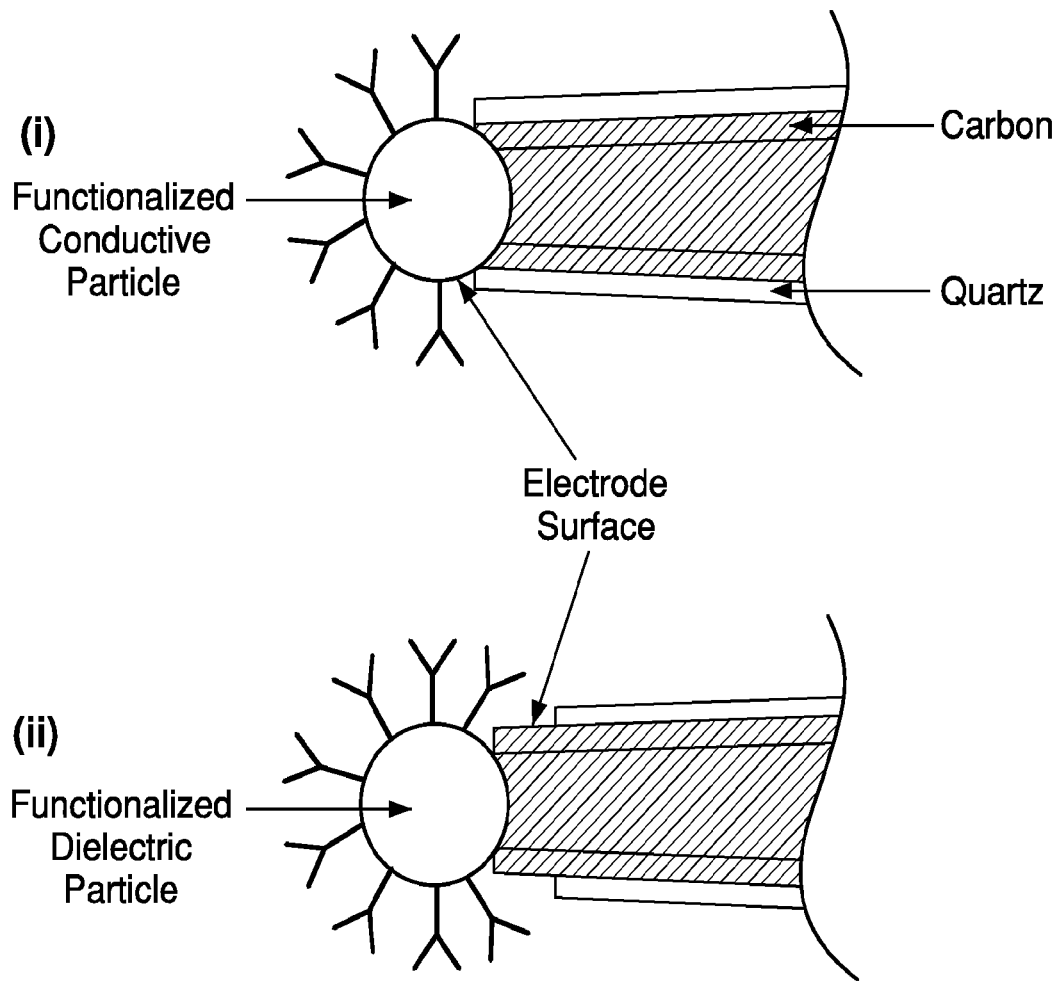
FIG. 6(*i*) illustrates a particle-tipped probe capped by a conductive particle where the particle acts as an electrode, FIG. 6(*ii*) illustrates a probe capped by a dielectric particle where the exposed carbon of the probe acts as an electrode.
Figure 7:
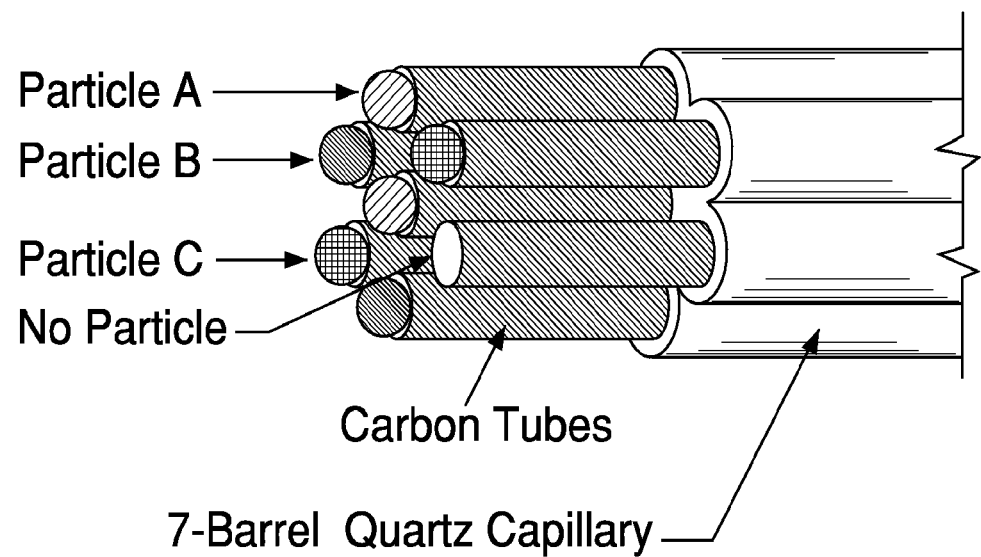
FIG. 7 illustrates a particle-tipped 7-electrode probe wherein particles A, B, and C are uniquely functionalized.

In other embodiments, the capillary is directly adjacent to a particle. An exemplary illustration of a particle positioned directly adjacent to a capillary is shown in FIGS. 6(i) and 6(ii), in which illustrations a particle is shown positioned directly adjacent to a capillary. FIG. 7 depicts multiple particles positioned directly adjacent to multiple carbon capillaries. Without being bound to any particular mode of operation, it is believed that particles seated on the end of a capillary are maintained in position by van der Waals forces.

It is contemplated that the capillaries and particles described herein may be combined so as to form a multiplexed device that comprises multiple, bundled capillaries sand multiple particles. Such a device is illustrated in FIG. 7, which figure depicts a seven-barreled quartz capillary from which seven carbonaceous capillaries extend.

Particles suitable for use in the claimed invention include conducting materials, semiconducting materials, insulating materials, and the like. Particles may also comprise a porous material, a nonporous material, or any combination thereof. Functionalized particles are available from, for example, Bangs Laboratories, Inc. (www.bangslabs.com, Fisher, Ind., USA). Suitable particles may be purchased commercially and modified by the user or, alternatively, synthesized by the user. Methods of selecting, synthesizing, and modifying particles will be known to those of ordinary skill in the art.

Suitable particles have a characteristic cross-sectional dimension in the range of from about 20 nm to about 200 microns, or in the range of from about 500 nm to about 50 microns. The optimal particle size for a given application will depend on the needs of the user and will be known to those of ordinary skill in the art. The size of a particle is preferably chosen such that the particle is capable of seating reliably on a capillary or other capture site.

Particles suitable for the present invention also include one or more functionalities. Suitable functionalities include antigens, antibodies, monomers, oligonucleotides, nucleic acids, ligands, enzymes, enzyme substrates, oligomers, dyes, fluorophores, and the like. Particle functionalities can be selected based on the analyte or analytes the device will be used to detect, and can be selected based on being complementary to the analytes. Particles can also be chosen based on size, shape, color, the presence of one or more fluorescent dyes of the particle, electrical resistance, or electrochemical properties. As discussed in further detail elsewhere herein, particle functionalities may be used to bind to target analytes and may also be used to identify a particle or its spatial location.

In one exemplary configuration, the capillary is connected to an electrical device. Suitable electrical devices include a meter capable of detecting electrical signals, a current source, a sensor, a controller, a computer, or any combination thereof. As a non-limiting example, a capillary may be electrically connected to a detector capable of observing changes in the resistance of the capillary when a particle becomes seated on the end of the capillary. Such a detector may be connected in turn to a computer capable of tracking and processing signals from one or more detectors so as to provide information about the positioning of particles across an array of capillaries or capture sites.

Figure 8:
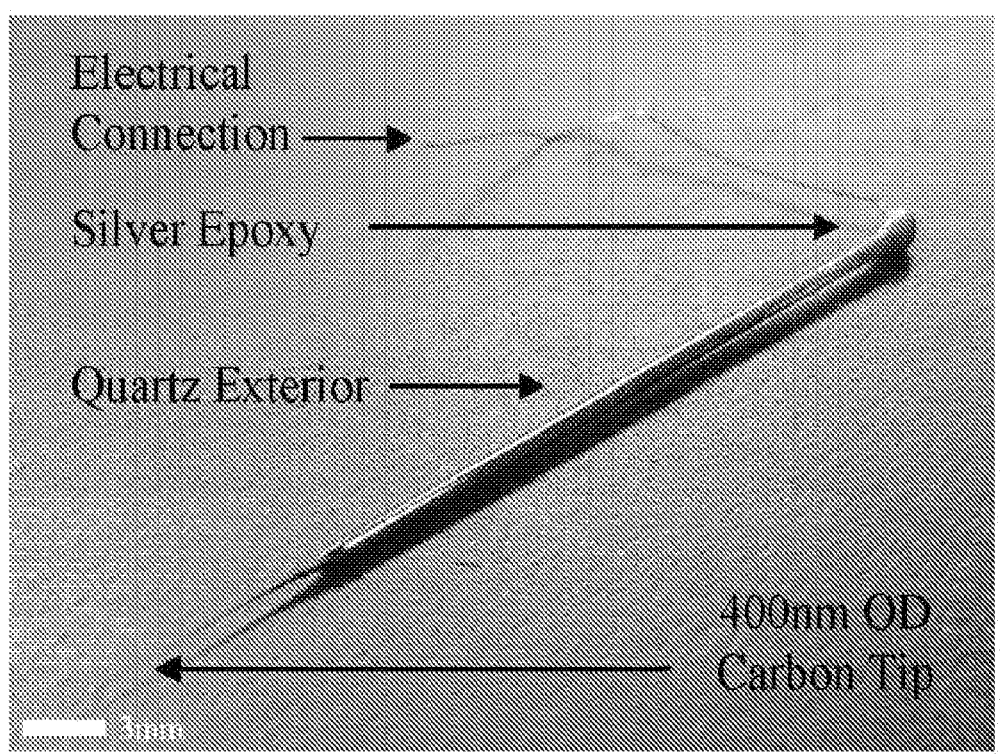
FIG. 8 depicts a hollow nanoscale carbon electrode protruding from a glass capillary with an electrical connection to the carbon electrode maintained by silver epoxy.

One sample configuration is illustrated in FIG. 8. That figure depicts a capillary electrical connection. As shown in FIG. 8, the electrical connection wire is maintained in contact with the conductive carbon capillary by silver epoxy. Other conductive materials known to those of ordinary skill in the art can be used to maintain such electrical connections. A given capillary or capture site may include two or more electrical connections to the same or different devices, depending on the needs of the user.

Electrode-particle assemblies can include electrodes adjacently assembled to various particles bearing different functionalities, which assemblies can be combined to form multiplexed devices. Such multiplexed devices are suitable for simultaneously detecting multiple analytes, where the analytes are complementary to the functionalities present on the particles. Such devices are capable of simultaneously detecting the presence of multiple analytes in a given sample. Arranging the capillaries in bundled form is considered especially suitable.

Also provided are devices, comprising: a substrate, wherein the substrate comprises a surface and at least one electrode, wherein at least one electrode is capable of being individually electrically addressed; and at least one particle comprising at least one functionality, wherein at least one particle comprising at least one functionality is adjacent to at least one electrode capable of being individually electrically addressed.

The at least one electrode capable of being electrically addressed is suitably capable of detecting a signal related the binding of one or more functionalities of the adjacent particle to one or more analytes. Such a signal is preferably electrical or magnetic in nature, but optical and radioactive signals are also contemplated.

Substrates comprise one or more materials capable of being shaped or formed. Dielectric materials, conductive materials, semiconductive materials, or any combination thereof are all considered suitable. Ceramics, polymers, alloys, insulated metals, or any combination thereof are suitable substrate materials, as are glass, quartz, silicon, alumina, tungsten, titanium, and the like.

The devices can include at least one electrode capable of being individually electrically addressed, adjacent to an indentation, cup, a bowl, a divot, a cavity, a disk, a stripe, a bump, or any combination thereof. Without being bound to any particular theory of operation, it is believed that positioning the electrode adjacent to a feature capable of accommodating one or more particles will allow for reliable positioning of particles relative to electrodes.

In some embodiments, at least one electrode capable of being individually electrically addressed electrode is characterized as recessed relative to the substrate surface or, in other embodiments, as being even or flush with the substrate surface. In other embodiments, the electrode may protrude above the substrate surface. In some embodiments, at least one electrode capable of being individually electrically addressed is itself characterized as an indentation, a cup, a bowl, a divot, a cavity, a disk, a stripe, a bump, or any combination thereof. Without being bound to any particular mode of operation, it is believed that shaping the electrode in a manner that allows the electrode to accommodate one or more particle can prevent, at least in part, particles from physically separating from adjacent electrodes.

In other embodiments, the electrode is a protuberance, a tube, a projection, and the like. The optimal shape of an electrode will be dictated by the needs of the user, and will be apparent to those of ordinary skill in the art.

Additional configurations include electrodes characterized as being in the form of capillaries. Tubular or straw-shaped electrodes are also suitable.

Figure 9:
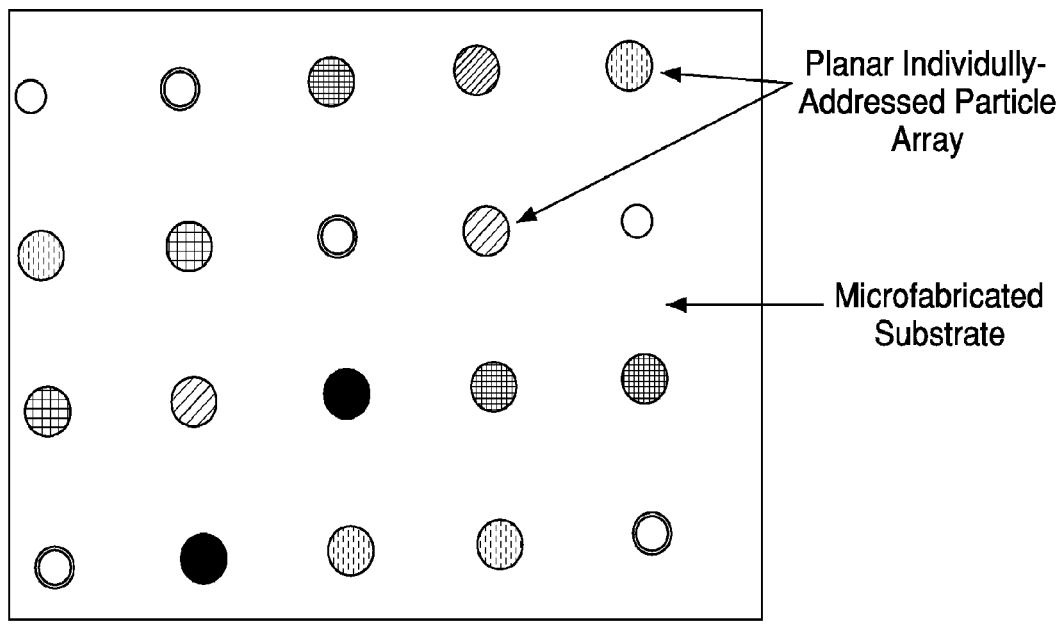
FIG. 9(*i*) illustrates an individually-addressed nanoelectrode array for electrochemical detection using a microfabricated planar substrate, and FIG. 9(*ii*) illustrates a cross-section of that array, note that electrical connections can be fabricated to connect with the conductive electrode lining.
Figure 9:
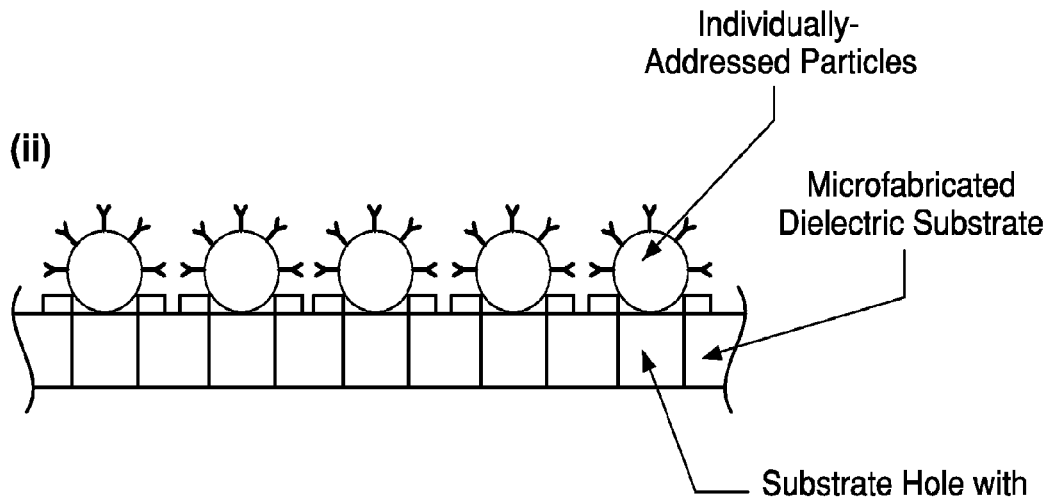

A schematic view of the disclosed devices is shown in FIG. 9. FIG. 9(i) depicts a view of a plurality of electrodes formed in a microfabricated substrate, wherein each of the electrodes can be individually electrically addressed. Such a device can be fabricated by photolithography techniques known to those practicing in the art. FIG. 9(ii) depicts a cross-section of one embodiment of the invention, which illustrates several individual electrodes directly adjacent to functionalized particles. Although FIG. 9 depicts electrodes as shells plated on the surfaces of holes, the electrodes, as described elsewhere herein, may be depressions, indentations, and the like.

Electrodes may be capillaries, having lumens in the range of from about 10 nm to about 100 micrometers. Electrodes of other forms—such as pits, depressions, divots, and the like—also suitably have a cross-sectional dimension in the range of from about 10 nm to about 100 micrometers. The dimensions of suitable particles are described elsewhere herein.

At least one electrode capable of being individually electrically addressed can include an electrical connection to a meter capable of detecting electrical signals, a current source, a controller, a computer, and the like.

In suitable embodiments, at least one electrode is capable of applying a current, an electric potential, a magnetic field, or any combination thereof. In some configurations, at least one electrode is capable of applying an alternating current, a direct current, a variable current, or any combination thereof.

In other embodiments, an electrode of the device is capable of applying a constant electric potential, an alternating electric potential, a variable electric potential, or any combination thereof. Similarly, electrodes are suitably capable of applying a constant magnetic field, a variable magnetic field, or any combination thereof.

Some embodiments include at least one particle comprising at least one functionality in electrical connection with at least one electrode capable of being electrically addressed. Suitable particles and functionalities are described elsewhere herein. As described elsewhere herein, devices may be assembled, at least in part, by applying a particular field or potential so as to direct particles bearing particular functionalities to particular locations.

Multiple electrode-particle assemblies, like those depicted in FIG. 9, can be used as multiplexed detector devices. Such multiplexed devices are suitable for simultaneously detecting multiple analytes, where the analytes are complementary to the functionalities present on the particles.

Also disclosed are methods for assembling devices, comprising: contacting a plurality of individually addressable and spatially distributed conductive capture electrodes with a plurality of particles dispersed in a carrier medium, wherein each of the particles comprises at least one sensing functionality, at least one barcode functionality, or any combination thereof; wherein contacting a conductive capture electrode with the plurality of particles dispersed in the carrier medium gives rise to at least one particle being positioned adjacent to at least one conductive capture electrode by action of capillary forces, surface forces, Van der Waals forces, electrokinetic forces, magnetic forces, electromagnetic forces, or any combination thereof; and identifying the spatial location of one or more particles positioned adjacent to at least one individually addressable and spatially distributed capture electrode.

In some embodiments, one or more particles positioned adjacent to at least one conductive capture electrode are in electrical connection with at least one conductive capture electrode.

A conductive capture electrodes can comprise a capillary. Suitable capillaries and their dimensions are described elsewhere herein, and may be fabricated by the methods of Bau, et al. The capillary is in electrical connection with a current source, a current meter, a voltage source, a voltage reader, a controller, a computer, a sensor, or any combination thereof.

The plurality of individually addressable and spatially distributed capture electrodes can comprise a substrate, wherein the substrate comprises one or more electrically conductive and individually electrically addressable sites acting as electrodes. Suitable forms and shapes for such sites are described elsewhere herein. In such embodiments, at least one of the electrically conductive sites is in electrical connection with a current source, a current meter, a voltage source, a voltage meter, a computer, a sensor, a controller, or any combination thereof.

Suitable particles are described elsewhere herein. Sensing functionalities comprise ligands, nucleic acids, enzymes, enzyme substrates, antibodies, oligonucleotides, antigens, oligomers, and the like.

Barcode functionalities can include physical characteristics that distinguish between particles, such as particle size, particle color, intensity of one or more fluorescent dyes of the particle, particle shape, particle electrical resistance, particle dielectric properties, particle magnetic properties, particle electrochemical properties, color of fluorescent dye of the particle, and the like.

Barcode functionalities also include biological functionalities such as ligands, nucleic acids, enzymes, enzyme substrates, antibodies, oligonucleotides, antigens, oligomers, and the like.

Contacting the electrodes with the particles can include the application of a potential or an external field, which include electrical potential, an electrical current, a magnetic potential, a pressure gradient, or any combination thereof.

The frequency of the field or potential is constant or varied. In some embodiments, two or more particles are affected differently by application of the potential. The particles may be affected on the basis of their surface charge, dielectric properties, or any combination thereof.

As a non-limiting example, a mixture of particles having different sensitivities to a potential of a particular frequency is exposed to that frequency. Under such conditions, the particles having a greater sensitivity to that frequency preferentially migrate along the direction of that potential toward capture sites, while the particles having a lesser sensitivity to that frequency remain essentially stationary.

In some embodiments, contacting the capillaries or capture sites with the particles gives rise to a change in a measurable quantity, which quantity is an electrical potential, an electrical current, a magnetic property, a dielectric property, a pressure, and the like. The change in a measurable quantity is suitably monitored and interpreted so as to provide information regarding the status of a particular capillary or capture site or electrode. As an example, a change in the dielectric property of a capture site indicates that one or more particles have become positioned adjacent to that site. Likewise, a change in the electrical resistance or capacitance of a capture site can also indicate that a particle has positioned adjacent to the site.

In some configurations, identifying the location of one or more particles adjacent to one or more conductive capture electrodes comprises: contacting the one or more particles positioned adjacent to at least one capture electrode with at least one reduction-oxidation effector species, wherein the reduction-oxidation effector species has a known reduction-oxidation potential; and monitoring one or more evolved threshold potentials necessary for reduction and oxidation reactions to take place. In these configurations, the threshold potential of the one or more particles positioned adjacent to at least one capture electrode is known and is compared to the evolved threshold potential affected by contacting the particles with the reduction-oxidation effector species. By comparing the evolved potential of electrode-adjacent particles of different known threshold potentials to the evolved potential at given electrode-adjacent particle, it is then determined which particle is adjacent to which electrode. By ensuring particles made of different materials also bear different functionalities, identifying the location of particular particles at particular electrodes in turn identifies which functionalities are present at those electrodes.

Identifying the spatial location of the one or more particles positioned adjacent to one or more conductive capture electrodes can include: contacting the one or more particles with a plurality of identifier agents, wherein at least one of the identifier agents is capable of binding uniquely to a particular type of barcode functionality; and monitoring one or more signals arising from the binding of at least one identifier agent to at least one barcode functionality. Suitable identifier agents comprise ligands, nucleic acids, enzymes, enzyme substrates, antibodies, antigens, oligomers, dyes, flurophores, oligonucleotides, or any combination thereof. Identifier agents are complementary to particle barcode functionalities, described elsewhere herein. The signals provided by these embodiments include an electrical signal, an optical signal, a magnetic signal, an electrochemical signal, a radioactive signal, or any combination thereof.

Identifying the spatial location of the particles can further comprise monitoring the voltage, current, impedance, resistance, or any combination thereof of the one or more particles adjacent to one or more conductive capture electrodes before, during, or after the binding of the identifier agent to the barcode functionality, so as to identify the spatial location of the one or more particles positioned adjacent to one or more conductive capture electrodes.

In other configurations, various types of identifier molecules, one type at a time, are brought into contact with particles adjacent to the conductive capture electrodes. By monitoring, on an electrode-by-electrode basis, the signals evolved from the interactions of identifier agents and the barcode functionalities of particles adjacent to electrodes, the locations of particular particles bearing particular barcode functionalities and particular sensing functionalities are determined. By knowing a priori which sensing functionalities and which barcode functionalities are present on particular particles, the spatial locations of particles bearing particular sensing functionalities may then be determined.

Where barcode functionalities comprise one or more physical characteristics of a particle, including particle size, particle color, the intensity of one or more fluorescent dyes of the particle, particle shape, particle electrical resistance, and particle electrochemical properties, the spatial locations of particles are determined by monitoring, on an electrode-by-electrode basis, electrical or optical signals evolved from the particles adjacent to electrodes. By a priori knowing the sensing functionalities of particular particles of particular barcode physical characteristics, the spatial locations of particles bearing particular sensing functionalities is then determined.

As one example, beads that are complementary to analyte A might bear a red fluorescent molecules, whereas beads that are complementary to analyte B might bear a green fluorescent molecules. In such an embodiment, once the beads are attached or proximate to capillaries or capture sites, the entire device may be fluorescently interrogated so as to determine the locations of those beads—and associated capture sites—that are complementary to analyte A (i.e., those beads that display a red fluorescence) and those that are complementary to analyte B. (i.e., those beads that display a green fluorescence). Once such a map of bead locations is generated, the device may then be contacted to an analyte-containing sample, and the presence of particular analytes may be determined by monitoring particular capture sites known to be associated with beads complementary to the analytes.

As will be apparent to those of ordinary skill in the art, there are innumerable permutations of barcode markers and functionalities that may be used on beads. By careful design, the user may assemble a broad library of particles bearing identifying functionalities, thus enabling the assembly of detector devices that may be customized to detect any number of targets or analytes.

It is envisioned that the plurality of electrodes is suitable for use as a multiplexed device capable of simultaneously detecting multiple analytes, wherein the analytes are complementary to the sensing functionalities present on particles in known spatial locations.

The disclosed inventions also include devices made according to the disclosed methods. Such a device is used as a probe, a sensor, a detector for a single analyte, a detector for multiple analytes, or any combination thereof. Such devices also include electronic, optoelectronic, or electromechanical devices, and the like.

Further provided are methods for assembling devices, comprising: contacting a first fluid with a plurality of conductive capture electrodes, wherein at least one of the conductive capture electrodes is capable of being individually electrically addressed; flowing a second fluid adjacent to the first fluid, wherein the second fluid resides between the first fluid and a director electrode and comprises a plurality of particles, wherein each of the particles comprise one or more functionalities; and applying an electric potential between the director electrode and the plurality of conductive capture electrodes so as to give rise to at least one particle of the second fluid being positioned adjacent to at least one conductive capture electrode.

It is contemplated that one or more particles of the second fluid positioned adjacent to at least one conductive capture electrode induce one or more electrical signals in at least one conductive capture electrode. Without being bound by any particular theory of operation, it is believed that the one or more particles positioned adjacent to at least one conductive capture electrode are maintained in position by capillary forces, surface forces, Van der Waals forces, electrostatic forces, electromagnetic forces, magnetic forces, chemical bonds, or any combination thereof.

Suitable conductive capture electrodes include capillaries. Suitable capillaries are described elsewhere herein.

In other embodiments, at least one conductive capture electrode is adjacent to an indentation, a bowl, a cup, a disk, a ring, a cylinder, a disk, a strip, or any combination thereof, or, in still other embodiments, at least one conductive capture electrode is directly adjacent to an indentation, a bowl, a cup, a disk, a ring, a cylinder, a disk, a strip, or any combination thereof.

At least one conductive capture electrode is in electrical connection with a current source, a meter capable of detecting an electrical signal, a computer, a controller, a sensor, or any combination thereof.

The method contemplates that the first fluid, second fluid, or both, flow relative to the plurality of conductive capture electrodes. The first and second fluid flows can be laminar, and are preferably characterized by low particle-based Reynolds numbers; such particle-based Reynolds numbers are less than about 1, or even less than about 0.1.

The first and second fluid layers can be characterized as having a thickness in the range of from about 50 microns to about 200 microns, or in the range of from about 100 to about 150 microns.

Suitable potentials include a DC electric field, an alternating electric field, a magnetic field, a pressure gradient, and the like.

The electrical potential is suitably less than about 5 volts, but other magnitudes may be suitable, depending on the user's needs and design constraints. In some embodiments, the electrical potential is periodic, irregular, or both. It is envisioned that the frequency of a potential ranges from about 1 to about 10 MHz.

Suitable particles and functionalities are described elsewhere herein.

The parameters of the first and second fluid flows and the sizes of the particles are each selected such that the positioning of the particles is governed by the electric potential and not governed by particle diffusion.

The method also includes monitoring one or more signals of the capture electrode while the electrode is in contact with the first and second fluids. These signals vary according to the position of the one or more particles relative to the conductive capture electrode. In some configurations, the signal may be a signal present only when a particle is adjacent to an electrode. Suitable signals include electrical signals, optical signals, mechanical signals, or any combination thereof.

The method further comprises terminating the potential to an individual electrode when the signal indicates at least one particle is positioned adjacent to at least one conductive capture electrode. The signal can include a change in resistance, in impedance, in optical intensity, in optical wavelength, or any combination thereof. The potential can be terminated so as to avoid the formation of a chain or particles.

Potentials may also include DC electric potential, an AC electric potential, a magnetic field, pressure field, or any combination thereof. The frequency of the potential may be varied.

The methods contemplate that one or more particles may be motivated on the basis of the electric charge of the particles. Particles are also motivated, in some embodiments, on the basis of a dielectric property of one or more of the particles, or even on the basis of a magnetic property of the one or more particles.

The disclosed methods further include changing the position of one or more positioned particles, which is accomplished by applying an electrical, magnetic, electromagnetic, or mechanical potential to the one or more positioned particles. Hence, in some embodiments, particles that have previously been positioned atop a capillary or adjacent to a capture site are then dislodged from that location by application of a potential. This enables the re-use of the capillaries or captures sites with a different set of beads, in turn enabling the construction of a broad range of detection devices, limited only by the functionalities contained within a given user's library of beads.

It is contemplated that the positioning of a particle adjacent to at least one conductive capture electrode gives rise to a change in a measurable quantity, which measurable quantity includes and electrical potential, an electrical current, a magnetic property, a dielectric property, a pressure, or any combination thereof. As discussed elsewhere herein, the change in a measurable quantity is suitably monitored and interpreted so as to provide information regarding the status of a particular capillary or capture site or electrode.

Also provided are devices made according to the method, wherein the devices are used as probes, sensors, detectors, or any combination thereof. Such devices can be electronic, optoelectronic, or electromechanical devices, or any combination thereof.

Figure 10:
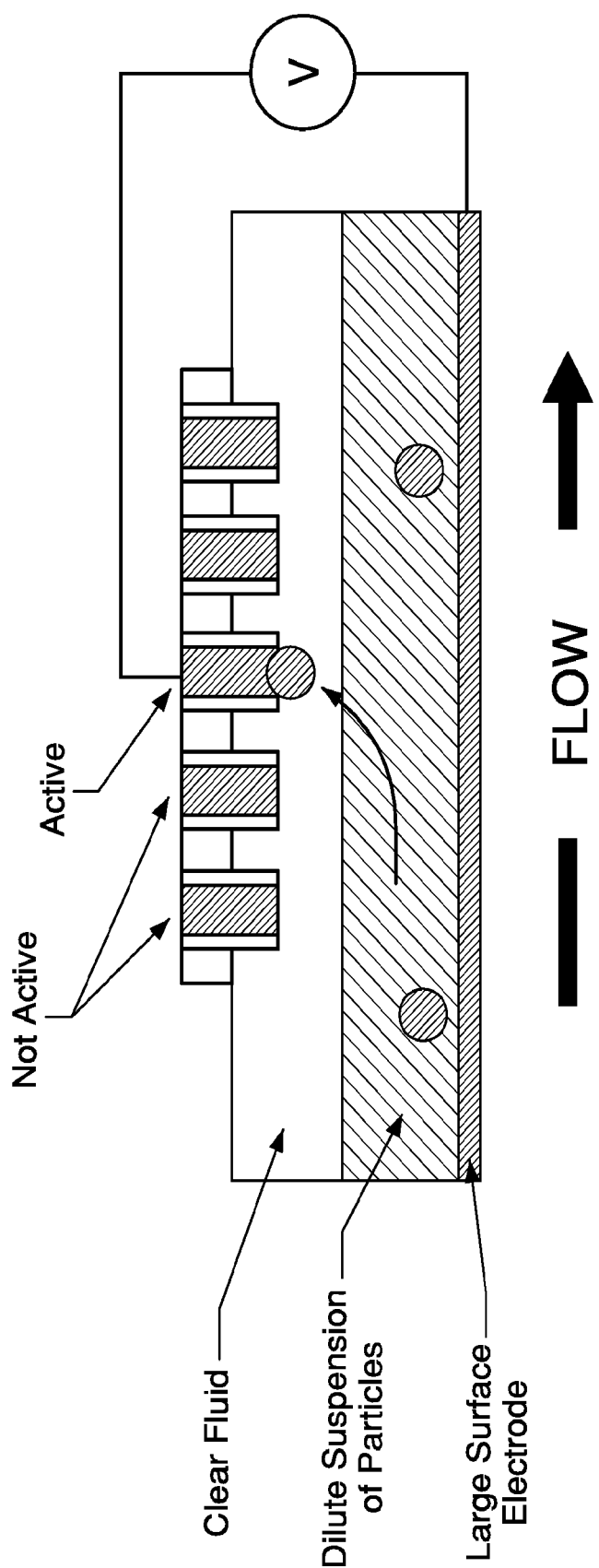
FIG. 10 is a schematic illustration of a electrokinetically-directed assembly of particles and electrodes (not to scale), in which particles in a separate dilute suspension are spatially separated from electrodes by a clear fluid, and the particles are attracted to the active electrode as the fluid laden with particles flows.

A depiction of the disclosed methods is shown in FIG. 10. The electric potential is applied between a known, active, conductive capture electrode and the large surface director electrode so as to motivate particle migration only to the active electrode. By introducing populations of particles bearing different, known functionalities one population at time and then activating known electrodes, a device is assembled wherein it is known which functionalities are present on specific particles on specific electrodes. Such devices are suitable for multiplexed detection of analytes complementary to the functionalities present on the particles adjacent to the individually electrically addressed electrodes.

EXAMPLES

Example 1

Figure 11:
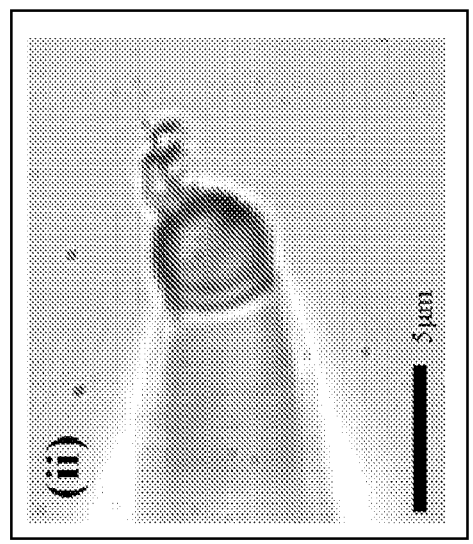
FIG. 11(*i*) illustrates a particle plugging the tip of a carbon nanoelectrode, and FIG. 11(*ii*) is an optical micrograph depicting a particle securely plugging the open end of a quartz micropipette.
Figure 11:
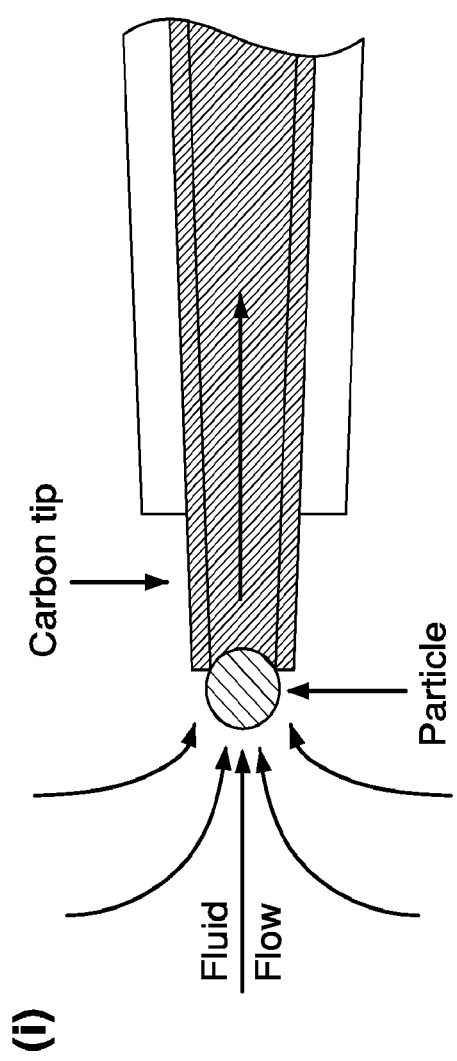

A carbon nano-capillary was brought into a contact with a dilute solution of suspended nanoparticles with diameters slightly larger than the inner diameter of the carbon capillary. The solution penetrated the carbon capillary by capillary suction and a particle locked into place by Van der Waals forces, as depicted in FIG. 11(*i*) (schematic view) and FIG. 11(*ii*) (actual image of particle—a magnetic bead—locked into place). Rigorous washings failed to detach the particle. Subsequently, the solvent trapped inside the bore of the carbon capillary evaporated. It was determined that either conducting or dielectric particles were suitable for this application. The process is applicable to mounting particles adorned with appropriate functionalities, e.g., ligands, antibodies or oligonucleotides.

Example 2

One method of fabricating the sensing devices of the instant invention is the directed assembly method. This method permits the positioning of particular particles adjacent or directly adjacent to particular electrodes, and eliminates the need for post-attachment analysis to determine which particles are adjacent to which electrodes.

The directed assembly can be performed using dielectrophoresis. To perform directed assembly, an electrode probe, such as a nano-scale capillary, is brought into contact with a dilute suspension of particles. A director electrode is then positioned opposite the electrode probe, and an alternating (AC) potential difference is applied between the nano-scale capillary and the director electrode. In the presence of the resulting, non-uniform electric field, one or more particles polarize and migrate towards the location of the maximum field intensity, at the opening of the nano-scale capillary. After the particle migrates to the nano-scale capillary, the particle locks into position by surface forces, as depicted in FIG. 11(*i*) and FIG. 11(*ii*).

Measures can be taken to prevent particles from reaching non-active electrodes by diffusion. To prevent diffusion-effected transport of particles, a microfluidic device, as shown in FIG. 10, is assembled. As shown, the device comprises a micro-conduit through which two fluid streams flow. The lower of the two streams is loaded with a low concentration of particles, and the upper of the two streams consists of particle-free fluid. A set of nano-scale capillaries is then contacted with the clear fluid, and due to the particles' low diffusivity and the laminar nature of the fluid flows, the particles do not migrate by themselves into the clear fluid. After the electric field is applied, one or more particles are attracted specifically to the activated electrode or electrodes.

The particle's attachment or positioning adjacent to an electrode is in turn sensed as an electrical signal. This signal opens the circuit that actuates the particular capillary to which the particle has attached. Deactivating the capillary in turn prevents one attached particle from acting as an electrode that attracts additional particles, and eliminates the possibility of chain formation. This method allows direction of a particle of known functionalization to a target capillary electrode and eliminates the need for subsequent registration (identification) of the particles.

Figure 12:
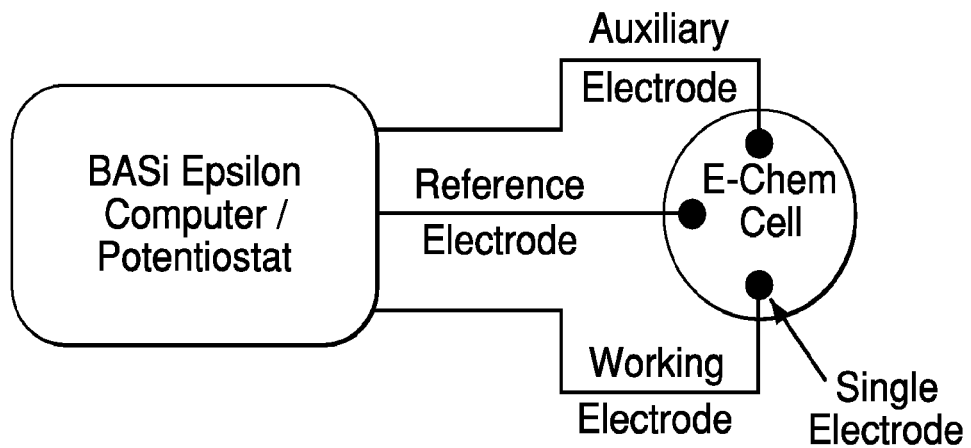
FIG. 12(*i*) is a schematic illustration of an embodiment of a system of the present invention for electrochemical analysis, FIG. 12(*ii*) is a schematic illustration comprising multiple nanoscale carbon electrodes on a single probe.
Figure 12:
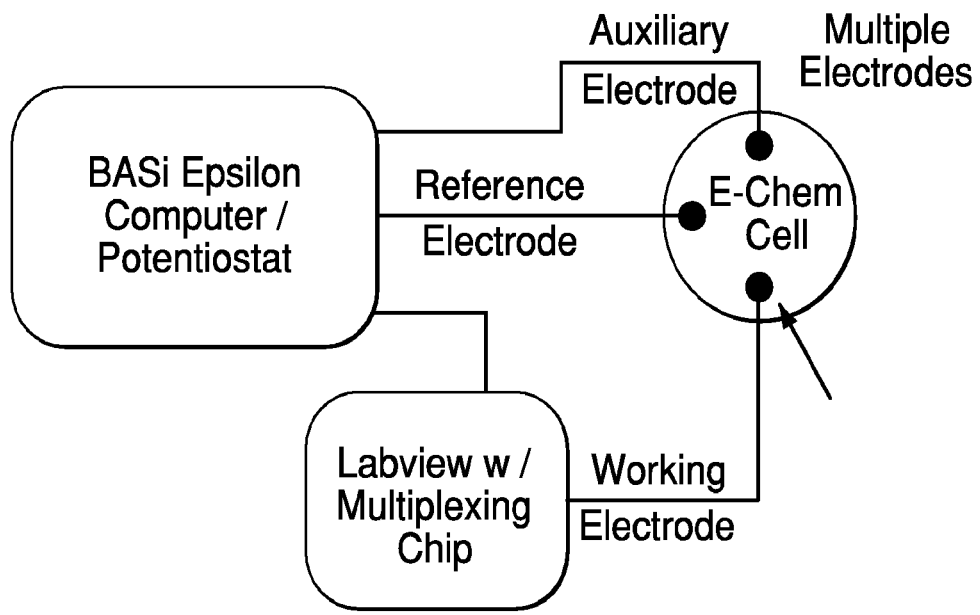

After the particle attaches to the capillary, the electrochemical characteristics of the capillary electrode-particle assembly are examined with a standard bench-top electrochemical analyzer, such as the potentiostat and associated electronics of the Epsilon benchtop electrochemical analyzer (BASi, Co.). See FIG. 12.

Identifying the particle through its electrochemical characteristics is also feasible. In one case, the particle's material is used as a barcode to identify a particle attached to an electrode. To this end, a particle-electrode assembly is inserted into an electrolyte solution containing reduction-oxidation species. The threshold potentials needed for reduction and oxidization reactions are measured and then correlated with the potentials known for the particle's material, thus identifying which particle has attached to which electrode in an array of electrodes. Particles made from various alloys and pure materials can be used.

Example 3

To characterize the electrochemical behavior of the particle-electrode sensors, the contact resistance between the functionalized particle and the carbon nanopipe and the overall resistance of the particle-tipped electrode is measured. The using the probe for electrochemical detection is tested by using a sandwich assay to detect various concentrations of avidin in solution. The microfluidic cell of Example 2 is exposed to flow of avidin solution at various dilutions. Subsequently, the sensor is then washed and the solution is replaced with biotinated enzyme. The biotin-enzyme complex then binds to the immobilized avidin. After a rigorous wash, a substrate to be processed by the enzyme is flowed across the bound enzyme complex, and the resulting electric current is detected. Such experiments establish the correlation between signal amplitude and analyte concentration. The experiments also provide an estimate of the sensitivity and detection limits of the sensor.

Example 4

To examine the multiplexing methods developed to perform multiple electrochemical measurements in a solution, nanoscale carbon multi-electrodes are formed by depositing carbon inside multi-barrel quartz micropipette substrates so as to form multiple carbon capillary electrodes. See FIG. 3(i) and FIG. 3(ii). Seven-barrel capillary tubes (1 mm OD, Sutter Co.) prefilled with iron catalyst can be used as the electrode-forming pipette template.

After undergoing a CVD process, the quartz is removed by wet-etching to expose the carbon tubes formed on their quartz tubes' inner diameters. Seven independent wires are attached with silver conductive epoxy to the tail end of each pipette probe to make electrical connections for electrochemical analysis.

After the carbon tubes are exposed, they are contacted with a dilute suspension of differently functionalized nanoparticles. The particles are positioned in place using the directed assembly methods described in Example 1 to position selected particles at the desired electrodes.

Following assembly of particles to electrodes, the particle-tipped electrodes are submerged in an aqueous solution containing anti-A, anti-B, and anti-C antibodies as shown in FIG. 7. A Labview-controlled multiplexing system switches the working electrode signals as the potentiostat and associated electronics of the Epsilon benchtop electrochemical analyzer scan and record electrochemical measurements. See FIG. 12. Differences in current traces are compared and analyzed to determine the detection of different analytes.

Example 4

A bundle of capillaries is contacted with a fluid comprising two different types of beads, each kind of bead (1) bearing a particular functionality that is uniquely complementary to a specific target and (2) each kind of being comprised of a material with a different set of dielectric properties that render that bead uniquely sensitive to a particular frequency of electricity.

By applying an electric field or current of a particular frequency, only those beads that react to such a frequency will migrate across the fluid to particular capillaries, after which migration the location of the migrated beads is catalogued. A second, different frequency is then applied to the fluid, which in turn causes migration of the other type of beads to unoccupied capillaries, and the location of these newly-migrated beads is then catalogued. Alternatively, different capillaries or capture sites may apply different electrical frequencies to the fluid, such that only a bead sensitive to a particular frequency will migrate to the capillary or capture site that applies that frequency. In such a configuration, successive application of different frequencies enables successive assembly of differently-functionalized beads onto specific capillaries. In this way, specifically-functionalized beads may be directed to specific capillaries or capture sites.

The user is then left with a device having beads in known locations that are specifically complementary to specific targets. Such a device is then useful for detecting the presence of known targets in a particular sample. Cups, electrodes, pits, protruberances, or other shapes and forms may be used in addition to or in place of capillaries.

Example 5

A bundle of capillaries is contacted to a fluid comprising magnetizable particles. A magnetic potential is effected across the fluid to the capillaries, such that one or more particles migrate to the capillaries and remain positioned on the capillaries by capillary forces or by effect of the magnetic field. In one embodiment, one or more capillaries is at least partially filled with a ferrofluid so as to effect attraction between the capillary and one or more particles.

Example 6

A device comprising magnetizable functionalized beads proximate to capillaries is assembled according to the disclosed methods. The user applies a magnetic potential oriented so as to dislodge the beads from the capillaries to separate the beads from the capillaries. The dislodged beads are then flushed away from the capillaries. The capillaries are the brought into contact with a new, different population of beads bearing particular functionalities, and a new detection device is assembled according to the methods of the present invention. In other configurations, the beads are dislodged by electric potential, or even by vibration.

In such configurations, a device may be assembled to detect target molecule A and B and is then used to detect—simultaneously—molecules A and B in a sample. After the detection of A and B is performed, the detector beads are dislodged and flushed away from the capillaries or electrodes, and the capillaries are then contacted with beads capable of detecting targets C and D, and a new device is then assembled, that is capable of detecting C and D. In such a way, the same set of capillaries may be used as the basis for a number of customizable, reusable detector devices by using the capillaries in conjunction with a library of beads that are complementary to any number of targets or analytes.

What is claimed is:

1. A sensing device, comprising:
    a substrate having a longest dimension and having a plurality of tubular apertures formed therein;
    at least some of the apertures having an interior sidewall surface;
    the substrate being characterized as an elongated capillary having an exterior surface;
    at least some of the tubular apertures penetrating through the entirety of the substrate in the longest dimension of the substrate;
    at least one of the apertures having an electrode disposed within the aperture that conforms to at least part of the interior sidewall surface of the aperture;
    at least one of the electrodes being individually addressable
    at least a portion of the exterior surface of the capillary being characterized as undulating in shape and at least partially conforming to the interior sidewall surface shape of at least one of the apertures; and
    at least one electrode defining a lumen having a diameter in the range of from about 10 nm to about 100 micrometers.

2. The sensing device of claim 1, wherein the substrate comprises a quartz capillary having a plurality of barrels, the plurality of barrels defining the plurality of apertures.

3. The sensing device of claim 1, wherein the substrate is characterized as having a planar surface and further wherein at least some of the plurality of apertures are formed in the planar surface.

4. The sensing device of claim 1, wherein at least one electrode comprises carbon.

5. The sensing device of claim 1, wherein at least one electrode is characterized as being formed along an interior sidewall surface of an aperture.

6. The sensing device of claim 1, wherein the substrate comprises a dielectric material.

7. The sensing device of claim 1, wherein at least one electrode is adjacent to an indentation, cup, a bowl, a divot, a cavity, a disk, a stripe, a bump, or any combination thereof, that is formed in the substrate.

8. The sensing device of claim 1, wherein at least one electrode is characterized as being even with a surface of the substrate.

9. The sensing device of claim 1, wherein at least one electrode is characterized as being recessed relative to a surface of the substrate.

10. The sensing device of claim 1, wherein at least one electrode is characterized as extending beyond a surface of the substrate.

11. The sensing device of claim 1, further comprising at least one particle positioned adjacent to an electrode.

12. The sensing device of claim 11, wherein the particle is characterized as being seated at the electrode.

13. The sensing device of claim 11, wherein the particle comprises at least one antigen, monomer, nucleic acid, ligand, enzyme, antibody, oligonucleotide, enzyme substrate, oligomer, dye, fluorophore, or any combination thereof.

14. The sensing device of claim 11, wherein the particle defines a cross-sectional dimension in the range of from about 20 nm to about 200 micrometers.

15. The sensing device of claim 1, further comprising a director electrode disposed external to the apertures.

16. The sensing device of claim 1, wherein at least one of the apertures has an electrode disposed within the aperture that conforms to substantially the entire circumference of the interior sidewall surface of the aperture.

17. A sensing device, comprising:
    a substrate having a planar surface and a thickness;
    the planar surface having at least one cross-sectional dimension that is larger than the thickness;
    the substrate having a plurality of apertures formed in the planar surface;
    at least some of the apertures having an interior sidewall surface;
    at least one of the apertures having an electrode disposed within the aperture that conforms to at least part of the interior sidewall surface of the aperture;
    at least one of the electrodes being individually addressable and defining a lumen having a diameter in the range of from about 10 nm to about 100 micrometers; and
    at least one electrode being characterized as being even with, or recessed relative to, the planar surface of the substrate.

18. The sensing device of claim 17, wherein at least one electrode is adjacent to an indentation, cup, a bowl, a divot, a cavity, a disk, a stripe, a bump, or any combination thereof, that is formed in the planar surface of the substrate.

19. The sensing device of claim 17, further comprising a director electrode disposed external to the apertures.

* * * * *